(12) United States Patent
Oliveira et al.

(10) Patent No.: US 9,150,886 B2
(45) Date of Patent: Oct. 6, 2015

(54) FOAM CONTROL OF ALCOHOLIC FERMENTATION PROCESSES

(75) Inventors: Abel Oliveira, Sao Paulo-SP (BR); Yuri Alencar Marques, Botucatu-SP (BR)

(73) Assignee: Dow Brasil Sudeste Industrial Ltda., Sao Paulo (BR)

(*) Notice: Subject to any disclaimer, the term of this patent is extended or adjusted under 35 U.S.C. 154(b) by 0 days.

(21) Appl. No.: 13/985,000

(22) PCT Filed: Mar. 7, 2012

(86) PCT No.: PCT/BR2012/000058
§ 371 (c)(1),
(2), (4) Date: Aug. 12, 2013

(87) PCT Pub. No.: WO2012/122613
PCT Pub. Date: Sep. 20, 2012

(65) Prior Publication Data
US 2014/0004585 A1    Jan. 2, 2014

Related U.S. Application Data

(60) Provisional application No. 61/452,367, filed on Mar. 14, 2011.

(51) Int. Cl.
*C12P 7/06* (2006.01)

(52) U.S. Cl.
CPC ... *C12P 7/06* (2013.01); *Y02E 50/17* (2013.01)

(58) Field of Classification Search
USPC ....................................................... 435/161
See application file for complete search history.

(56) References Cited

U.S. PATENT DOCUMENTS

| 4,836,951 A | 6/1989 | Totten et al. |
| 5,567,606 A | 10/1996 | Hayashi et al. |
| 6,083,998 A * | 7/2000 | Romualdo et al. ............ 516/117 |
| 2007/0275122 A1 | 11/2007 | Cazaroto et al. |

FOREIGN PATENT DOCUMENTS

| WO | 01/41909 A1 | 6/2001 |
| WO | 2010/036555 A2 | 4/2010 |

OTHER PUBLICATIONS

Romio et al, 2005, retrieved from Internet: http://www.ucs.br/ucs/tplJovensPesquisadores2006/pesquisa/jovenspesquisadores2006/trabalhos_pdf/vida/tiagoromio.pdf [retrieved on Jul. 31, 2012.
Pelton, Journal of Industrial Microbiology & Biotechnology (2002), 29, pp. 149-154.
Junker, Biotechnol. Prog., 2007, 23, pp. 767-784.
K.G. Marinova, et al., Bulg. J. Phys, 39 (2012), pp. 53-64, "Impact of Surface Structure on the Foaming/Defoaming Performance".
Sarah J. Routledge, et al., Microbial Cell Factories, 2011, 10:17, pp. 1-11, "Antifoam addition to shake flask cultures of recombinant Pichia pastoris increases yield".

* cited by examiner

*Primary Examiner* — Robert Yamasaki
*Assistant Examiner* — Teresa E Knight
(74) *Attorney, Agent, or Firm* — Whyte Hirschboeck Dudek S.C.

(57) ABSTRACT

The method of producing bioethanol by sugarcane fermentation is improved by using a polyalkylene glycol with a hydroxyl functionality of greater than 2 as a foam controlling agent.

8 Claims, 3 Drawing Sheets

FOAM CONTROL OF ALCOHOLIC FERMENTATION PROCESSES

BACKGROUND OF THE INVENTION

1. Field of the Invention

This invention relates to foam control. In one aspect, the invention relates to foam control in an aqueous, alcoholic fermentation process while in another aspect, the invention relates to foam control in an aqueous, alcoholic fermentation process using a polyalkylene glycol with high functionality.

2. Description of the Related Art

Foam generation is a major problem in the production of alcohol-based fuels produced through fermentation, e.g., sugarcane bioethanol. Propylene oxide (PO)/ethylene oxide (EO) diols have been used as foam control agents in these applications for many years. These antifoam agents, however, often exhibit low persistency which requires their repeated addition to the fermentation broth to keeping foaming under control. As such, a continuing interest exists for antifoam agents with higher persistency which means, in turn, that they can be used in less frequently thus simplifying the process and, possibly, lowering costs.

SUMMARY OF THE INVENTION

In one embodiment the invention is a method of controlling foaming of an aqueous, alcoholic fermentation broth during a fermentation process, the method comprising the step of adding to the broth a foam controlling amount of a polyalkylene glycol with a functionality (f) of greater than (>) 2, preferably equal to or greater than (≥) 3, or ≥4, or ≥5, or ≥6.

DETAILED DESCRIPTION OF THE PREFERRED EMBODIMENT

Definitions

Figure 1:
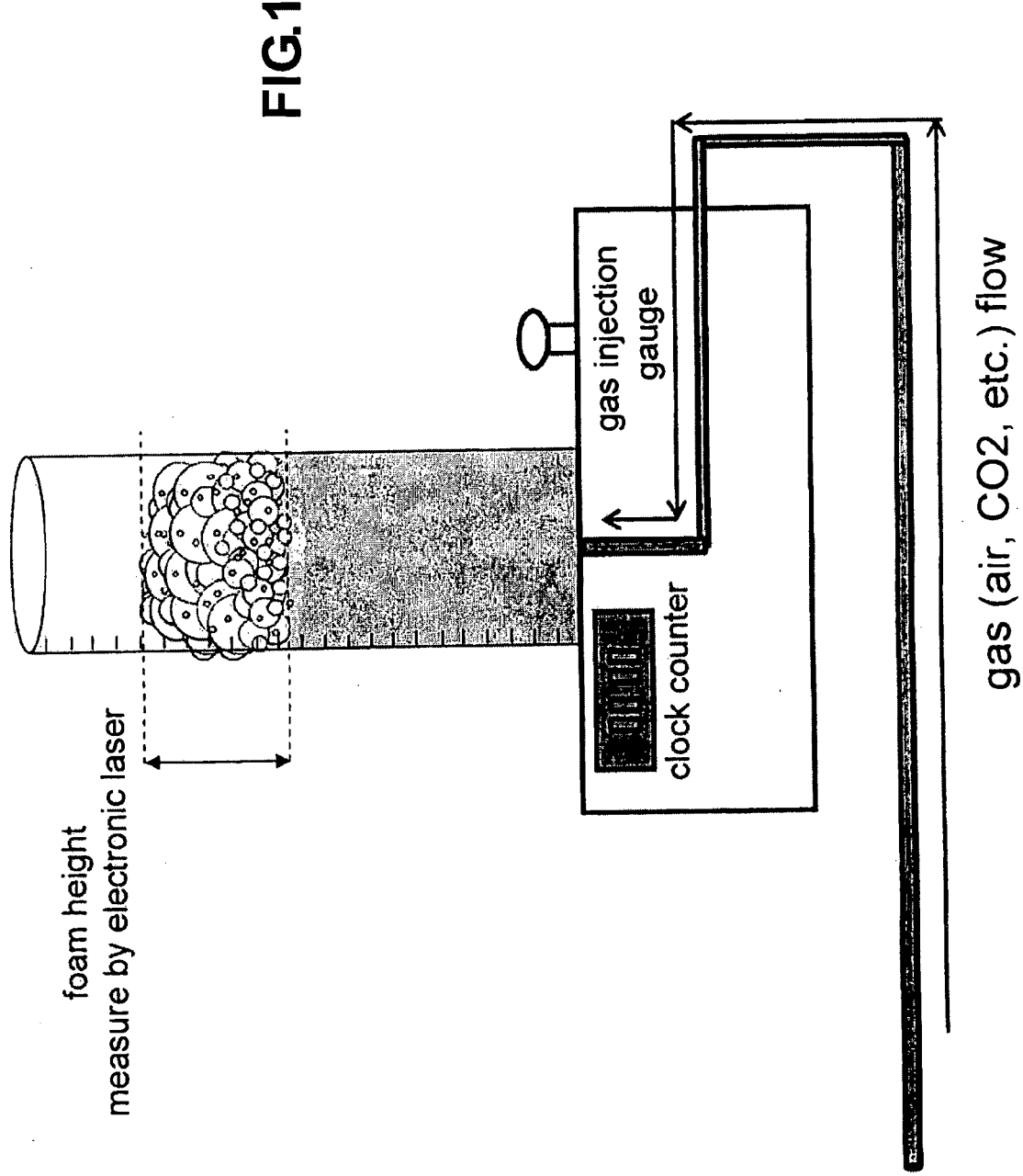
FIG. 1 illustrates an experimental apparatus for measuring foam height in a laboratory simulated sugarcane bioethanol production.

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, etc., is from 100 to 1,000, then all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amount of foam controlling agent added to the fermentation broth.

"Broth" and like terms means a liquid medium containing a variety of nutrients which is used to grow cultures of bacteria or other microorganisms.

"Fermentation" and like terms means an anaerobic, cellular process in which organic foods are converted into simpler compounds, and chemical energy is produced.

"Functionality", "f", and like terms refers to the number of terminal hydroxyl groups on the PAG molecular chain.

DETAILED DESCRIPTION OF THE INVENTION

Polyalkylene Glycol (PAG)

The polyalkylene glycols used in the practice of this invention are made by the polymerization of an alkylene oxide monomer or a mixture of alkylene oxide monomers initiated by a polyhydric compound, and promoted by a base catalyst, e.g., potassium hydroxide, under reactive conditions known in the art with specific compositions based on modifications of known compounds (see, for example, "Alkylene Oxides and Their Polymers", Surfactant Science Series, Vol. 35). Upon the completion of the polymerization, the reaction mixture is vented and then neutralized by the addition of one or more acids, e.g., acetic acid. Optionally, the salts resulting from the neutralization, e.g., potassium acetate salts, can be removed by any known means, e.g., filtration. The neutralized polyalkylene glycol product has a pH value of 4.0 to 8.5.

In one embodiment the initiator is a polyhydric compound with a functionality of >2, preferably ≥3, or ≥4, or ≥5, or ≥6. Examples of such initiators include but are not limited to glycerin, trimethylolpropane, sorbitol, pentaerythritol, sucrose and any mixture of the same.

The PAG of this invention can be prepared by a variety of methods known in the art. In one embodiment, the PAG is prepared by base-catalyzed alkoxylation. The base is typically at least one of an alkali or alkaline earth metal hydroxide or carbonate, aliphatic amine, aromatic amine, or a heterocyclic amine. In one embodiment, sodium or potassium hydroxide is the base catalyst. In one embodiment the PAG is neutralized with a carboxylic acid, e.g., acetic acid. In one embodiment the soluble acid salts, e.g., potassium acetate salts, are left in the PAG while in another embodiment, the salt is filtered out or otherwise removed from the PAG. In one embodiment the PAG is prepared by acid-catalyzed alkoxylation.

The alkylene oxide used as the monomer in the polymerization is a $C_2$ to $C_8$ oxide, such as ethylene oxide, propylene oxide, butylene oxide, hexene oxide, or octene oxide. In one embodiment, the alkylene oxide is ethylene or propylene oxide.

In one embodiment of this invention the polyalkylene oxide is polyethylene oxide, or a polypropylene oxide, or a water soluble copolymer of ethylene oxide (EO) and propylene oxide (PO), or a mono methyl, ethyl, propyl, or butyl ether of one of them, initiated by glycerol, sorbitol or sucrose.

In one embodiment the polyalkylene oxide is a copolymer of EO and PO in which units derived from EO comprise from 10 to 35 weight percent (wt %), typically from 15 to 30 wt % and more typically from 19 to 27 wt %. In one embodiment, the polyalkylene glycol has a molecular weight (weight average, Mw) of 100-10,000 grams per mole (g/mol), more typically 1,000-6,000 g/mol. Exemplary, commercially available PAG with an f>2 include but are not limited to VORANOL™ RN482, VORANOL™ 466 and VORANOL™ 370 polyether polyols available from The Dow Chemical Company.

The PAG of this invention is used in known ways and in known amounts. It is used in a foam controlling amount, i.e., in an amount sufficient to control the level of foam in a fermentation liquor, i.e., broth, at or below a desired level during the fermentation process. Typically it is used in an amount of 1 to 1,000 parts per million (ppm), more typically 3 to 50 ppm. The PAG can be added continuously or intermittently to the liquor. In one embodiment the PAG is added to the fermentation liquor at 5 to 250 microliters per liter of liquor every 10 to 60 minutes.

The PAG of this invention can be added neat, i.e., alone, or in combination with one or more other materials such as, without limitation, solvents, stabilizers, antioxidants, fillers and other foam control agents. Representative of these other materials are PAG with a functionality of 2 or less, silicones, silica, hydrocarbon oil, vegetable oil and the like.

Fermentation Broth

Aqueous, alcohol fermentation processes are well known in the art. While the PAG foam control agents of this invention are particularly well suited for sugarcane bioethanol fermentation processes, these foam control agents are also useful in other fermentation processes including, but not limited to, the production of biofuels from sugar beets, cereal grain, potato, manioc and the like.

The invention is further illustrated by the following examples.

Specific Embodiments

FIG. 1 illustrates an experimental apparatus for measuring foam height in a laboratory simulated sugarcane bioethanol production. Foam height is measured on the glass scale or by an electronic laser. Gas (air, carbon dioxide, etc.) is injected through a porous plate to promote bubbling/foaming in the broth.

Figure 2:
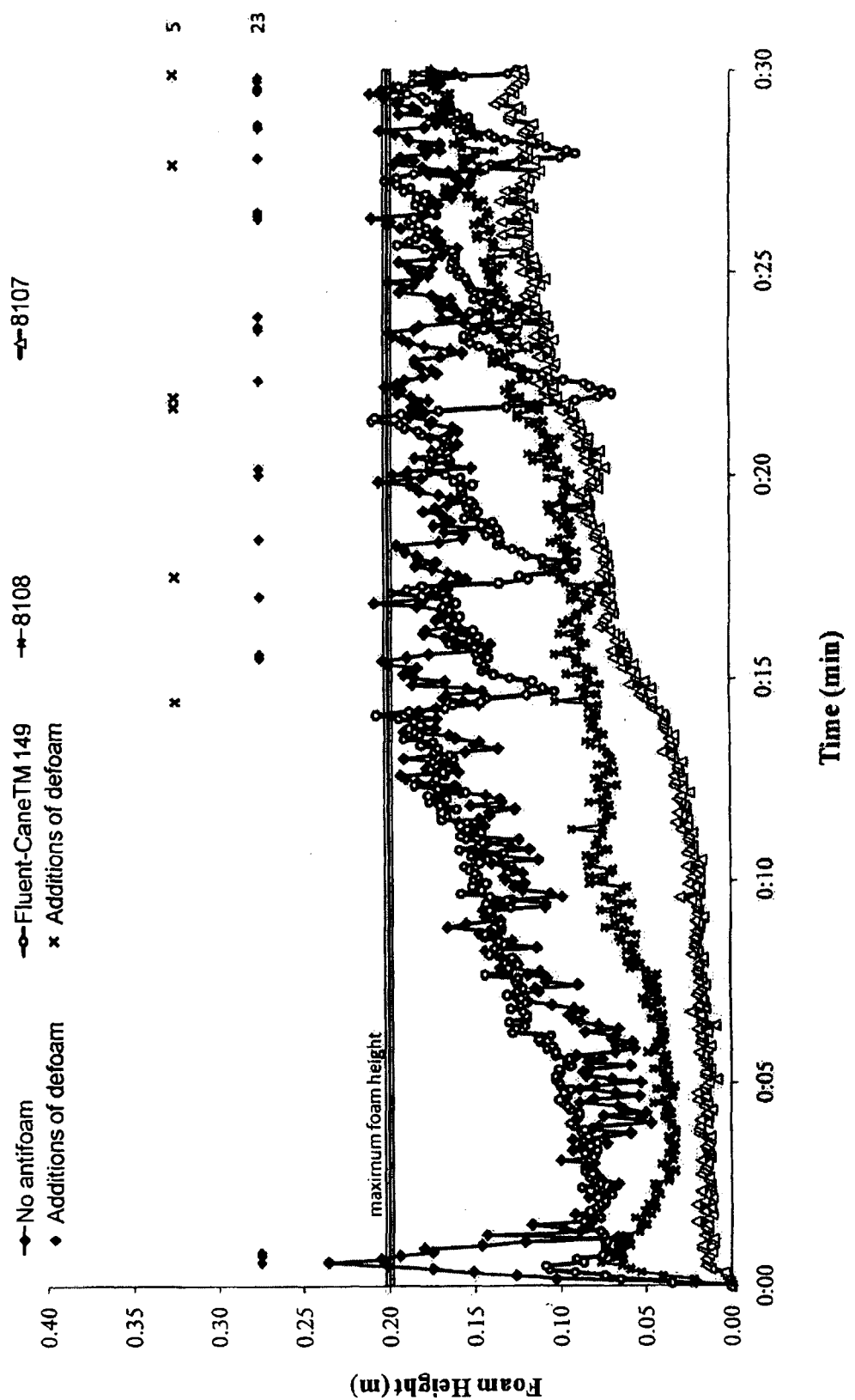
FIG. 2 is a graph reporting the results of a first test of a bioethanol foam control study.
Figure 3:
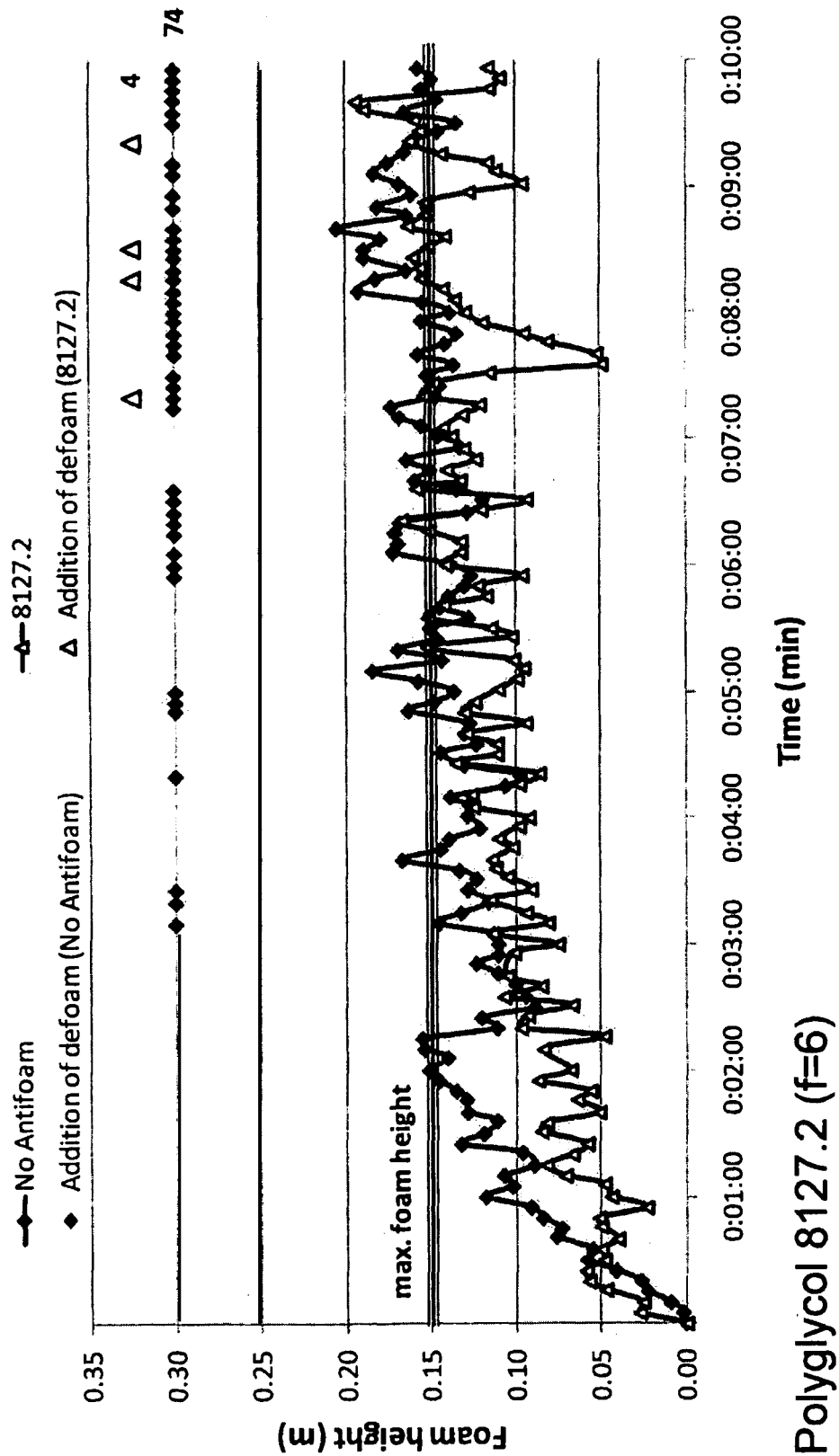
FIG. 3 is a graph reporting the results of a second test of a bioethanol foam control study.

Prior to bioethanol fermentation, a foam control agent is added to the fermentation broth to minimize foam formation during the fermentation process. Once the foam reaches a certain height, a defoamer such as mineral oil is added to again reduce the foam below a certain level. Each time the foam height reaches a certain level, more defoamer is added to again reduce the foam to the desired height. Measuring foam height and the required number of additions of defoamer in this manner permits one to gauge the efficacy of a foam control agent. The results are reported in FIGS. 2 and 3 and Tables 1 and 2. For the results reported in FIG. 2 and Table 1, 5.5 ppm of defoamer was added to the simulated broth. For the results reported in FIG. 3 and Table 2, 1 ppm of defoamer was added to the simulated broth.

TABLE 1

Results of the Addition of 5.5 ppm Antifoam to a Fermentation Broth Comprising Molasses, Yeast and Ethanol

| Foam Control Agent (Antifoam) | Defoamer Number of Additions |
|---|---|
| None | 23 |
| FLUENT-CANE ™ 149 with f < 2 | 5 |
| PO/EO$^1$ with f = 3 | 0 |
| PO/EO$^2$ with f = 3 | 0 |

FLUENT-CANE ™ 149 is a PO/EO copolymer mono propylene glycol initiated and propoxylated until 1750 g/mol molecular weight with EO capping and comprising 25 wt % EO, and available from The Dow Chemical Company.
PO/EO$^1$ is a copolymer glycerin initiated and propoxylated until 3,000 g/mol molecular weight with EO capping and comprising 25 wt % EO, and available from The Dow Chemical Company.
PO/EO$^2$ is a copolymer glycerin initiated and propoxylated until 3,000 g/mol molecular weight with EO capping and comprising 20 wt % EO, and available from The Dow Chemical Company.

TABLE 2

Results of the Addition of 1 ppm Antifoam to a Fermentation Broth Comprising Molasses, Yeast and Ethanol

| Foam Control Agent (Antifoam) | Defoamer Number of Additions |
|---|---|
| None | 74 |
| PO/EO$^3$ with f = 6 | 4 |

PO/EO$^3$ is a copolymer propoxylated until 5,000 g/mol molecular weight with EO capping and comprising 27 wt % EO, and available from The Dow Chemical Company.

The PAG with functionality greater than 2 demonstrated efficient foam reduction performance, observed by lower foam height achieved in the foaming test as well as less defoamer additions. The PAG with functionality greater than 2 showed improved foam reduction performance against commonly used PAG with lower functionality.

Although the invention has been described with certain detail through the preceding description of the preferred embodiments, this detail is for the primary purpose of illustration. Many variations and modifications can be made by one skilled in the art without departing from the spirit and scope of the invention as described in the following claims.

What is claimed is:

1. A method of controlling foaming of an aqueous, alcoholic broth fermentation during a fermentation process, the method comprising the step of adding to the broth a foam controlling amount of a polyalkylene glycol (PAG) with a functionality (f) of greater than (>) 2 wherein the PAG is a propylene oxide/ethylene oxide (PO/EO) copolymer.

2. The method of claim 1 in which the propylene oxide/ethylene oxide copolymer has an EO content of 10 to 35 weight percent (wt %).

3. The method of claim 2 in which the PAG has a weight average molecular weight of 100-10,000 grams per mole (g/mol).

4. The method of claim 3 in which the PAG is added to the fermentation broth in an amount of 1 to 1,000 parts per million (ppm).

5. The method of claim 4 in which the functionality is greater than (>) 3.

6. The method of claim 1 in which the PAG is added to the fermentation broth at the start of the fermentation process.

7. The method of claim 1 in which the PAG is added to the fermentation broth intermittently over the fermentation broth.

8. The method of claim 1 in which the fermentation broth comprises liquid from sugarcane.

* * * * *